(12) United States Patent
Silva

(10) Patent No.: US 8,153,842 B2
(45) Date of Patent: Apr. 10, 2012

(54) METHOD FOR PRODUCING 3-(2,2,2-TRIMETHYL-HYDRAZINIUM) PROPIONATE DIHYDRATE

(76) Inventor: Jorge Silva, Riga (LV)

( * ) Notice: Subject to any disclaimer, the term of this patent is extended or adjusted under 35 U.S.C. 154(b) by 183 days.

(21) Appl. No.: 12/310,385

(22) PCT Filed: Sep. 4, 2006

(86) PCT No.: PCT/EP2006/065945
§ 371 (c)(1),
(2), (4) Date: Feb. 20, 2009

(87) PCT Pub. No.: WO2008/028514
PCT Pub. Date: Mar. 13, 2008

(65) Prior Publication Data
US 2009/0318731 A1    Dec. 24, 2009

(51) Int. Cl.
*C07C 227/00* (2006.01)
*C07C 241/00* (2006.01)
*C07C 243/00* (2006.01)

(52) U.S. Cl. .................................. 562/554; 562/560

(58) Field of Classification Search .................. None
See application file for complete search history.

(56) References Cited

U.S. PATENT DOCUMENTS
2,259,726 A * 10/1941 Borglin .................. 530/221

OTHER PUBLICATIONS

Delaney, Drug Discovery Today, Predicting Aqueous Solubility From Structure, 2005, 10(4), pp. 289-295.*

* cited by examiner

*Primary Examiner* — Paul A Zucker
(74) *Attorney, Agent, or Firm* — Colin P. Abrahams

(57) ABSTRACT

A method for producing 3-(2,2,2-trimethylhydrazinium)propionate dihydrate by saponification of salts of 3-(2,2,2-trimethylhydrazinium)propionate esters with subsequent purification step using saturation with carbon dioxide or sulphur dioxide in alcoholic solution.

12 Claims, No Drawings

METHOD FOR PRODUCING 3-(2,2,2-TRIMETHYL-HYDRAZINIUM) PROPIONATE DIHYDRATE

The invention relates to a process for the preparation of pharmaceutically active compounds, namely to the pharmaceutically active substance 3-(2,2,2-trimethylhydrazinium) propionate dihydrate, the known medicine Meldonium (INN) of formula (1)

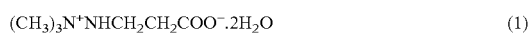

$$(CH_3)_3N^+NHCH_2CH_2COO^-.2H_2O \quad (1)$$

Meldonium is a cardiovascular medicine with average daily dose 1.0 g. Because this preparation is used as an over-the-counter drug, a need for an inexpensive large scale manufacturing process is needed. Known processes for the preparation of Meldonium are not convenient for large scale production.

Therefore the aim of this invention are improvements in the method for manufacturing Meldonium known hitherto allowing lower production costs and application for large scale manufacturing processes.

A number of processes for the preparation of compound of the formula (1) is known. A common scheme is used hitherto to produce this compound: starting with 1,1-dimethylhydrazine and esters of acrylic acid 3-(2,2-dimethylhydrazino)propionic acid is prepared, which is alkylated by an appropriate alkylating agent (methyl chloride, methyl bromide, methyl iodide, dimethylsulphate etc.). The halide or methylsulphate of alkyl-3-(2,2,2-trimethylhydrazinium)propionate thus obtained is subjected to hydrolysis and deionisation. Known methods for the preparation of Meldonium differ by the approach to hydrolysis and/or deionisation of the corresponding 3-(2,2,2-trimethylhydrazinium)propionate salt.

Thus a method is known, according to which solution of halide or methylsulphate of alkyl-3-(2,2,2-trimethylhydrazinium)propionate is treated with a strongly basic ion exchange resin, exchanging acid anion for hydroxyl anion, followed by spontaneous alkaline hydrolysis (U.S. Pat. No. 4,481,218). The method has many disadvantages: strongly basic ion exchangers are unstable and undergo decomposition and oxidation during processing; they withstand only a limited number of regeneration cycles; large quantities or solvents, acids and bases as well as deionised water are needed to regenerate the resins; low ion exchange capacity and therefore high production costs of compound (1) by this process are typical. This process is not convenient for large scale production of Meldonium.

Some of the disadvantages mentioned above are avoided if alkyl-3-(2,2,2-trimethylhydrazinium)propionate salt is deionized by electrodialysis. This process in production of Meldonium is applied in two different technical solutions (SU 1262900, RU 1262900, LV 5046 and Vasilyev V. N., Omel'chenko Y. N., Tkach I. N., Pugovic O. V., Kaivins I. J. Electromembrane synthesis of 3-(2,2,2-trimethylhydrazinium)propionate. *Zhurnal Prikladnoj Khimii* (*Journal of Applied Chemistry*, Rus), 1992, issue. 12, vol. 65, pp. 2823-2825).

The disadvantage of this process is a need for highly specialised equipment with enhanced requirements to the corrosion resistance of constructive materials used (platinum plated titanium electrodes, controlled diameter pore membrane, mechanical and chemical stability of membrane material, ceramic coated constructive elements of the electrodialysis equipment). The main parameters of electrodialysis process have to be experimentally adapted—current, flow speed, concentration of solutions, distances between electrodes, form of the camera etc. Because of membrane pollution during the production process, the parameters initially set should be constantly changed. The membrane undergoes degradation during the process as well and has to be replaced regularly. Therefore the maintenance costs of such equipment are high and the scaling-up of the process is complicated. Simultaneously with dialysis electrolysis takes place and explosive gases are produced that cause safety problems. Therefore producing Meldonium using electrodialysis is also rather expensive.

An alternative process of Meldonium production is known, according to which in the first step 1,1-dimethylhydrazine is condensed with acrylic acid trimethylsilyl ester and the resulting product is alkylated to halogenide of 3-(2,2,2-trimethylhydrazinium)propionate trimethylsilyl ester (RU 95118258.04). This approach is based on the well known fact that trimethylsilylesters of carboxylic acids undergo spontaneous hydrolysis in water even without alkaline catalysis. The main disadvantage of this process is considerably high costs of trimethylsilyl esters of acrylic acid compared with methyl acrylate.

A Standard method of alkaline hydrolysis of carbonic acid esters in case of an alkyl-3-(2,2,2-trimethylhydrazinium)propionate salt could not be successfully realised till now because of the problems of separation of 3-(2,2,2-trimethylhydrazinium)propionate dihydrate and the resulting inorganic salts. It is known that 3-(2,2,2-trimethylhydrazinium) propionate forms various double salts (SU 849724, Lopyrev V. A., Dolgushin G. V., Voronkov M. G. Applied chemistry of 1,1-dimethylhydrazine and its derivatives. *Zhurnal Prikladnoj Khimii* (*Journal of Applied Chemistry*, Rus), 1998, issue. 8, vol. 71, pp. 1233-1248). Some of them are very stable and can be used in agriculture as pesticides.

Our attempts to separate such double salts, for example double salt of NaCl and 3-(2,2,2-trimethylhydrazinium)propionate, present in the crude 3-(2,2,2-trimethylhydrazinium) propionate dihydrate obtained by hydrolysis of an alkyl-3-(2,2,2-trimethylhydrazinium)propionate chloride by simple dissolving or heating the product in alcohol were unsuccessful. As the result some of NaCl still remained in the product as the double salt and all attempts to prepare pure 3-(2,2,2-trimethylhydrazinium)propionate dihydrate (with content of the main substance>99.5%) failed. We have prepared pure 3-(2,2,2-trimethylhydrazinium)propionate double salt, for example, with NaI by treating ethyl 3-(2,2,2-trimethylhydrazinium)propionate iodide with sodium ethylate and established that it can be crystallized from ethanol without separation into constituents. Due to high solubility of 3-(2,2,2-trimethylhydrazinium)propionate dihydrate in water, this solvent also can not be used for separation of the inorganic salt constituent.

A summary of solubilities of inorganic double salts was recently published (C. H. Yoder, J. P. Rowand, Application of the simple salt lattice energy approximation to the solubility of minerals. American Mineralogist, Volume 91, pages 747-752, 2006). The solubilities of the double salts are similar to the solubilities of the less soluble constituent salts or lie between the solubilities of the constituent salts. Therefore standard crystallization is not the method of choice for separation of the double salt constituents. It is known that double salts can be separated into their constituents by multiple fractional crystallizations at different temperatures. While such approach can be used for inorganic salts, it is not useful for medicines due to risk of decomposition of the labile organic component.

Surprisingly, we have now found that double salts of 3-(2,2,2-trimethylhydrazinium)propionate with the inorganic salts formed in the hydrolysis process can be completely separated, if the reaction solution in alcohol during precipitation of inorganic salts had been saturated with gaseous acid anhydride, namely carbon dioxide or sulphur dioxide. For example, the double salt of 3-(2,2,2-trimethylhydrazinium) propionate with KBr can thus be separated into its constituents and the inorganic salt can be completely removed from 3-(2,2,2-trimethylhydrazinium)propionate by a simple filtration. According to this approach 3-(2,2,2-trimethylhydrazinium)propionate dihydrate can be prepared and purified to pharmaceutical grade (>99.5%) by using conventional methods of purification (crystallisation).

The present process can be conveniently used for conversion of alkyl-3-(2,2,2-trimethylhydrazinium)propionate chloride, bromide or methyl sulphate, as well as other easily hydrolysable ester of 3-(2,2,2-trimethylhydrazinium)propionate salt, for example—benzyl-3-(2,2,2-trimethylhydrazinium)propionate salt. The amounts of alkaline agent can be used from equimolar ratio to more then double excess of the base, preferably 1.05-2.1 counted on 3-(2,2,2-trimethylhydrazinium)propionate ester salt.

This approach can be also used for conversion such intermediates as halide or methyl sulphate of 3-(2,2,2-trimethylhydrazinium)propionic acid. In this case esters of 3-(2,2,2-trimethylhydrazinium)propionate halide or methyl sulphate can be hydrolized under acidic conditions with catalysis by HCl, sulphuric acid, phosphoric acid etc., followed by neutralisation by an appropriate inorganic base (for example—sodium, potassium, calcium or magnesium hydroxide or another appropriate base, for example sodium, potassium, lithium or caesium carbonate or bicarbonate etc.) and the double salts thus obtained can be easily separated by the invented process using saturation of the solution with carbon dioxide or sulphur dioxide.

The invented method for producing 3-(2,2,2-trimethylhydrazinium)propionate dihydrate provides for the object of this invention—to develop a convenient and inexpensive large scale manufacturing process of the target compound, which differs from known processes by the separation of 3-(2,2,2-trimethylhydrazinium)propionate double salts using carbon dioxide or sulphur dioxide, which has a number of advantages over the known processes. Thus, the novel method involves use of inexpensive and available reagents (sodium, potassium hydroxide or another appropriate base, carbon dioxide or sulphur dioxide, ethanol or 2-propanol), easily available and common chemical technology equipment (reactors, vessels for crystallisation, centrifuges etc.). Said process is fast and gives high yields of high purity 3-(2,2,2-trimethylhydrazinium)propionate dihydrate or Meldonium (>99.5%) after simple crystallisation. Therefore the invented process enables to inexpensively produce high quality Meldonium.

The examples below serve to illustrate the present invention. However, they are in no way to be regarded as limiting.

EXAMPLES

The ethanol used in the following examples, if not mentioned otherwise, was commercial ethanol, containing approximately 95% by volume of ethanol and 5% of water.

Example 1

66.8 g of KOH (content of the main substance 90%) were suspended in 450 ml of ethanol and, at 18-20° C. 120.5 g of methyl-3-(2,2,2-trimethylhydrazinium)propionate bromide were added during 5-10 min under stirring. The stirring was continued at 18-20° C. until ester saponification was complete (controlled by TLC). The mixture was then cooled to 2-4° C., and saturated with $CO_2$ to pH 8.1-8.5. The precipitate thus formed was filtered off, washed with 3×20 ml of ethanol and the combined filtrates were evaporated. 89 g (92%) of semi-crystalline solid was obtained (3-(2,2,2-trimethylhydrazinium)propionate content 94%). Crystallization from ethanol or 2-propanol or another appropriate solvent gave 3-(2,2,2-trimethylhydrazinium)propionate dihydrate with m.p. 85-87° C. (purity>99.5%).

Example 2

34.0 g of KOH (content of the main substance 90%) were suspended in 450 ml of ethanol and at 18-20 C., 120.5 g of methyl-3-(2,2,2-trimethylhydrazinium)propionate bromide during 5-10 min were added under stirring. The stirring was continued at 18-20° C. until ester saponification was complete (controlled by TLC). The mixture was then cooled to 2-4° C., and saturated with $CO_2$ to pH 8.1-8.5. The precipitate thus formed was filtered off, washed with 3×20 ml of ethanol and combined filtrates were evaporated. 90 g (93%) of semi-crystalline solid were obtained (3-(2,2,2-trimethylhydrazinium)propionate content 93%. Crystallization from ethanol or 2-propanol or another appropriate solvent gave 3-(2,2,2-trimethylhydrazinium)propionate dihydrate with m.p. 85-87° C. (purity>99.5%).

Example 3

66 g of KOH (content of the main substance 90%) were suspended in 450 ml of ethanol and, at 18-20° C., 136 g of methyl-3-(2,2,2-trimethylhydrazinium)propionate methylsulphate were added under stirring during 5-10 min. The stirring was continued at 18-20° C. until the ester saponification was complete (controlled by TLC). The mixture was then cooled to 2-4° C., saturated with $CO_2$ to pH 8.1-8.5. Precipitate thus formed was filtered off, washed with 3×10 ml of ethanol and the combined filtrates were evaporated. 89.5 g (89%) of semi-crystalline solid was obtained. Crystallization from ethanol or 2-propanol or another appropriate solvent gave 3-(2,2,2-trimethylhydrazinium)propionate dihydrate with m.p. 85-87° C. (purity>99.5%).

Example 4

66 g of KOH (content of the main substance 90%) are suspended in 450 ml of ethanol and, at 18-20° C., 136 g of methyl-3-(2,2,2-trimethylhydrazinium)propionate methylsulphate were added under stirring during 5-10 min. The stirring was continued at 18-20° C. until the ester saponification was complete (controlled by TLC). The mixture was then cooled to 2-4° C., precipitate thus formed was filtered off and washed with 2×20 ml of ethanol. Filtrates were combined and saturated with $CO_2$ to pH 8.1-8.5. Precipitate thus formed was filtered off, washed with 3.times.10 ml of ethanol and the combined filtrates were evaporated. 89.5 g (89%) of semi-crystalline solid were obtained (3-(2,2,2-trimethylhydrazinium)propionate content 91%) and finally purified by electrodialysis. After evaporation the solid was crystallized from ethanol or 2-propanol or another appropriate solvent and gave 3-(2,2,2-trimethylhydrazinium)propionate dihydrate with m.p. 85-87° C. (purity>99.5%).

Example 5

24 g of NaOH were suspended in 450 ml of ethanol and, at 18-20° C., 136 g of methyl-3-(2,2,2-trimethylhydrazinium)

propionate chloride during 5-10 min were added under stirring. The stirring was continued at 18-20° C. until ester saponification was completed (controlled by TLC). The mixture was then cooled to 2-4° C. and saturated with $CO_2$ to pH 8.1-8.5. Precipitate thus formed was filtered off, washed with 3×10 ml of ethanol and the combined filtrates were evaporated. 91 g (95%) of semi-crystalline solid were obtained (3-(2,2,2-trimethylhydrazinium)propionate content 95%). Crystallization from ethanol or 2-propanol or another appropriate solvent gave 3-(2,2,2-trimethylhydrazinium)propionate dihydrate with m.p. 85-87° C. (purity>99.5%).

Example 6

33 g of NaOH were suspended in 450 ml of ethanol and, at 18-20° C., 92 g of methyl-3-(2,2,2-trimethylhydrazinium)propionate chloride during 5-10 min were added under stirring. The stirring was continued at 18-20° C. until ester saponification was completed (controlled by TLC). The mixture was then cooled to 2-4° C. and saturated with $CO_2$ to pH 8.1-8.5. Precipitate thus formed was filtered off, washed with 3×10 ml of ethanol and the combined filtrates were evaporated. 95 g (95%) of semi-crystalline solid were obtained (3-(2,2,2-trimethylhydrazinium)propionate content 95%). During crystallization from 2-propanol strongly basic ion exchange resin Amberlite IRA-400 is added in amount corresponding to 1.2 equivalents of $Cl^-$ remaining, after 5 min the resin is filtered off, washed with 20 ml of ethanol and the combined filtrates cooled. 3-(2,2,2-trimethylhydrazinium)propionate dihydrate with m.p. 85-87° C. (purity>99.5%) is obtained.

Example 7

33 g of KOH (content of the main substance 90%) are suspended in 450 ml ethanol and, at 18-20° C., 113.5 g of methyl-3-(2,2,2-trimethylhydrazinium)propionate bromide were added under stirring during 5-10 min. The stirring was continued at 18-20° C. until ester saponification was complete (controlled by TLC). The mixture was then cooled to 2-4° C., inorganic precipitate thus formed was filtered off and washed with 2×20 ml of ethanol. Filtrates were combined and saturated with $SO_2$ to pH 8.1-8.5. Precipitate formed was filtered off, washed with 3×10 ml of ethanol and the combined filtrates were evaporated. 90 g (93%) of semi-crystalline solid were obtained (3-(2,2,2-trimethylhydrazinium)propionate content 94%) and finally purified by electrodialysis. The solid obtained after evaporation was crystallized from ethanol or 2-propanol or another appropriate solvent and gave 3-(2,2,2-trimethylhydrazinium)propionate dihydrate with m.p. 85-87° C. (purity>99.5%).

Example 8

66 g of KOH (content of main substance 90%) were suspended in 450 ml of ethanol and, at 18-20° C., 136 g of methyl-3-(2,2,2-trimethylhydrazinium)propionate bromide were added under stirring during 5-10 min. The stirring was continued at 18-20° C. until ester saponification was completed (controlled by TLC). The mixture was then cooled to 2-4° C., inorganic precipitate thus formed was filtered off and washed with 2×20 ml of ethanol. Filtrates were combined and saturated with $SO_2$ to pH 8.1-8.5. Precipitate thus formed is filtered off, washed with 3×10 ml ethanol and the combined filtrates were evaporated. 89 g (92%) of semi-crystalline solid were obtained (3-(2,2,2-trimethylhydrazinium)propionate content 94%). Crystallization from ethanol or 2-propanol or another appropriate solvent gave 3-(2,2,2-trimethylhydrazinium)propionate dihydrate with m.p. 85-87° C. (purity>99.5%).

Example 9

Ethyl 3-(2,2,2-trimethylhydraziniumpropionate iodide was refluxed with 2 equivalents of sodium ethylate in absolute ethanol for 20 hours, cooled, the precipitate filtered off, extracted with boiling methanol, the solution evaporated and the residue crystallized from absolute ethanol. Colourless crystals of the double salt of 3-(2,2,2-trimethylhydrazinium)propionate and sodium iodide were obtained, m.p. 186-188° C.

The invention claimed is:

1. Process for preparing 3-(2,2,2-trimethylhydrazinium)propionate dihydrate from a salt of 3-(2,2,2-trimethylhydrazinium) propionate esters by saponification with an alkaline agent, followed by precipitation of inorganic salts by saturating the reaction mixture in organic solvent with gaseous acid anhydride and isolating the target compound by known methods.

2. Process of claim 1 wherein said salt is halide.

3. Process of claim 1 wherein said salt is methyl sulphate.

4. Process of claim 1 wherein one of said esters is methyl ester.

5. Process of claim 1 wherein one of said esters is ethyl ester.

6. Process of claim 1 wherein said alkaline agent is selected from the group, consisting of sodium, potassium, lithium, caesium, calcium and magnesium oxides, hydroxides, carbonates and bicarbonates.

7. Process of claim 1 wherein said alkaline agent is used in molar ratio 1.05-2.15 to said salt.

8. Process of claim 1 wherein said alkaline agent is potassium hydroxide.

9. Process of claim 1 wherein said alkaline agent is sodium hydroxide.

10. Process of claim 1 wherein said organic solvent is selected from the group consisting of methanol, ethanol and 2-propanol.

11. Process of claim 1 wherein said acid anhydride is carbon dioxide.

12. Process of claim 1 wherein said acid anhydride is sulphur dioxide.

* * * * *